US012226194B2

(12) United States Patent
Zeng et al.

(10) Patent No.: US 12,226,194 B2
(45) Date of Patent: Feb. 18, 2025

(54) METHOD, APPARATUS AND SYSTEM FOR EVALUATING CARDIAC DIASTOLIC FUNCTION

(71) Applicant: SHENZHEN DARMA TECHNOLOGY CO., LTD., Guangdong (CN)

(72) Inventors: Lingjun Zeng, Shenzhen (CN); Zhengpei Chu, Shenzhen (CN); Pengbo Liu, Shenzhen (CN); Shaochun Zhuang, Shenzhen (CN)

(73) Assignee: CARDIOSTORY INC., Lewes, DE (US)

( * ) Notice: Subject to any disclaimer, the term of this patent is extended or adjusted under 35 U.S.C. 154(b) by 582 days.

(21) Appl. No.: 17/613,475

(22) PCT Filed: May 20, 2019

(86) PCT No.: PCT/CN2019/087640
§ 371 (c)(1),
(2) Date: Nov. 22, 2021

(87) PCT Pub. No.: WO2020/232606
PCT Pub. Date: Nov. 26, 2020

(65) Prior Publication Data
US 2022/0218208 A1  Jul. 14, 2022

(51) Int. Cl.
*A61B 5/02* (2006.01)
*A61B 5/00* (2006.01)
(Continued)

(52) U.S. Cl.
CPC ............ *A61B 5/021* (2013.01); *A61B 5/0205* (2013.01); *A61B 5/0261* (2013.01); *A61B 5/11* (2013.01);
(Continued)

(58) Field of Classification Search
CPC ..... A61B 5/0205; A61B 5/021; A61B 5/0261; A61B 5/11; A61B 5/366; A61B 5/7239; A61B 5/7267
See application file for complete search history.

(56) References Cited

U.S. PATENT DOCUMENTS

| | | | |
|---|---|---|---|
| 2016/0089031 A1* | 3/2016 | Hu | ............... A61B 5/1116 600/479 |
| 2018/0289288 A1 | 10/2018 | Kim et al. | |
| 2019/0175072 A1* | 6/2019 | Schmidt | ............... A61B 5/7271 |

FOREIGN PATENT DOCUMENTS

| CN | 101801263 A | 8/2010 |
|---|---|---|
| CN | 108056769 A | 5/2018 |

(Continued)

*Primary Examiner* — Amanda K Hulbert
(74) *Attorney, Agent, or Firm* — Cheng-Ju Chiang

(57) ABSTRACT

A method for evaluating cardiac diastolic function, which applies to the field of cardiac monitoring. The method comprises: obtaining vibration information of the surface of the thoracic cavity of a subject by means of one or more optical fiber sensors; preprocessing the vibration information to generate hemodynamic related information; performing high-frequency component extraction on the hemodynamic related information to generate high-frequency component information; determining a first feature value and a second feature value based on the hemodynamic related information and the high-frequency component information; generating indicating parameters based on the first feature value and the second feature value, and evaluating the cardiac diastolic function of the subject based on the indicating parameters.

14 Claims, 7 Drawing Sheets

(51) Int. Cl.
*A61B 5/0205* (2006.01)
*A61B 5/021* (2006.01)
*A61B 5/026* (2006.01)
*A61B 5/11* (2006.01)
*A61B 5/366* (2021.01)

(52) U.S. Cl.
CPC ............ *A61B 5/366* (2021.01); *A61B 5/7239* (2013.01); *A61B 5/7267* (2013.01)

(56) References Cited

FOREIGN PATENT DOCUMENTS

| | | |
|---|---|---|
| CN | 109310371 A | 2/2019 |
| WO | 2012/149652 A1 | 11/2012 |

\* cited by examiner

METHOD, APPARATUS AND SYSTEM FOR EVALUATING CARDIAC DIASTOLIC FUNCTION

CROSS REFERENCE TO RELATED APPLICATIONS

The present application is a 35 U.S.C. § 371 National Phase conversion of International (PCT) Patent Application No. PCT/CN2019/087640, filed on May 20, 2019, the disclosure of which is incorporated by reference herein. The PCT International Patent Application was filed and published in Chinese.

FIELD OF THE INVENTION

The present invention relates to the field of cardiac monitoring, and particularly relates to a non-invasive method, apparatus, and system for evaluating cardiac diastolic function.

BACKGROUND OF THE INVENTION

Heart failure (abbreviated as HF) is a clinical syndrome with multiple etiologies and pathogenesis. With the aging of the population and an increasing survival rate of patients with acute myocardial infarction, the number of patients with chronic heart failure is increasing rapidly. Patients with heart failure suffer from a chronic state to an acute worsening state, and suffer from an accompanied elevated filling pressure. Elevated filling pressure will cause the heart's function to enter a rapid vicious circle, but the patient itself will not feel the symptoms until the filling pressure continues to rise for about 20 days and need to be admitted to the hospital urgently; while at this time, the impairment of the heart function is caused and is irreversible. When the patient is identified in an elevated filling pressure status, timely intervention is required to avoid further deterioration. This has become the consensus of clinicians.

At present, there are implantable products used to evaluate the diastolic function, but the cost is relatively high, and if it is only used for monitoring, patients are less likely to accept. Therefore, a more friendly and more convenient product is needed for monitoring the diastolic function.

SUMMARY OF THE INVENTION

Technical Problem

An object of the present invention is to provide a method, device, system, and computer-readable storage medium for evaluating cardiac diastolic function of a subject; and aims to realize a non-invasive evaluation of the cardiac diastolic function.

Solutions to the Problem

Technical Solutions

In a first aspect, the present invention provides a method for evaluating cardiac diastolic function, comprising steps of:
  acquiring vibration information on a body surface corresponding to thoracic cavity of a subject by means of one or more fiber-optic sensors, where the one or more fiber-optic sensors are placed under the body of the subject;
  preprocessing the vibration information to generate hemodynamic related information;
  performing high-frequency component extraction on the hemodynamic related information to generate high-frequency component information;
  determining a first characteristic value and a second characteristic value based on the hemodynamic related information and the high-frequency component information; where the first characteristic value represents an event of aortic valve opening during the ventricular ejection, and the second characteristic value represents an event that blood flows into the left ventricle and impacts the left ventricular wall in the early ventricular diastole;
  generating indicating parameters based on the first characteristic value and the second characteristic value, and evaluating the cardiac diastolic function of the subject based on the indicating parameters.

In a second aspect, the present invention provides a computer-readable storage medium having computer programs stored thereon, which when being executed by a processor, cause the processor to perform the steps of the above-mentioned method for evaluating cardiac diastolic function.

In a third aspect, the present invention provides a device for evaluating cardiac diastolic function, comprising: one or more processors; a memory; and one or more computer programs, wherein the one or more computer programs are stored in the memory, and configured to be executed by the one or more processors; and the one or more processors execute the one or more computer programs to perform the steps of the above-mentioned method for evaluating cardiac diastolic function.

In a fourth aspect, the present invention provides a system for evaluating cardiac diastolic function, comprising:
  one or more vibration sensors, configured to be placed under the subject's body to obtain the subject's vibration information; and
  the device for evaluating cardiac diastolic function, as described above, connected to the one or more vibration sensors.

Advantages of the Preset Invention

Advantages

The method of the present invention monitors the diastolic function by acquiring the vibration information of the subject without intruding his body, it is a passively measuring, and can realize continuous monitoring. The subject only needs to lie on the measuring device to perform the measurement, and no need for professional assistance. The method has the advantages of high measurement accuracy and simple operation, can improve the comfort of the tester, and can be applied to scenes such as hospitals and homes. The diastolic function assessment system provided in the present invention can evaluate the diastolic function of the subject, and then prompt a warning in advance when deterioration appear, so as to help the subject avoid deterioration.

DETAILED DESCRIPTION OF THE INVENTION

In order to make the objects, technical solutions, and advantages of the present invention clearer, the present invention will be further described in detail below in conjunction with the accompanying drawings and embodiments. It should be understood that the specific embodiments described here are only used to explain the present invention, but not to limit the present invention.

In order to illustrate the technical solutions of the present invention, the following is explained through specific embodiments.

First Embodiment

Figure 1:
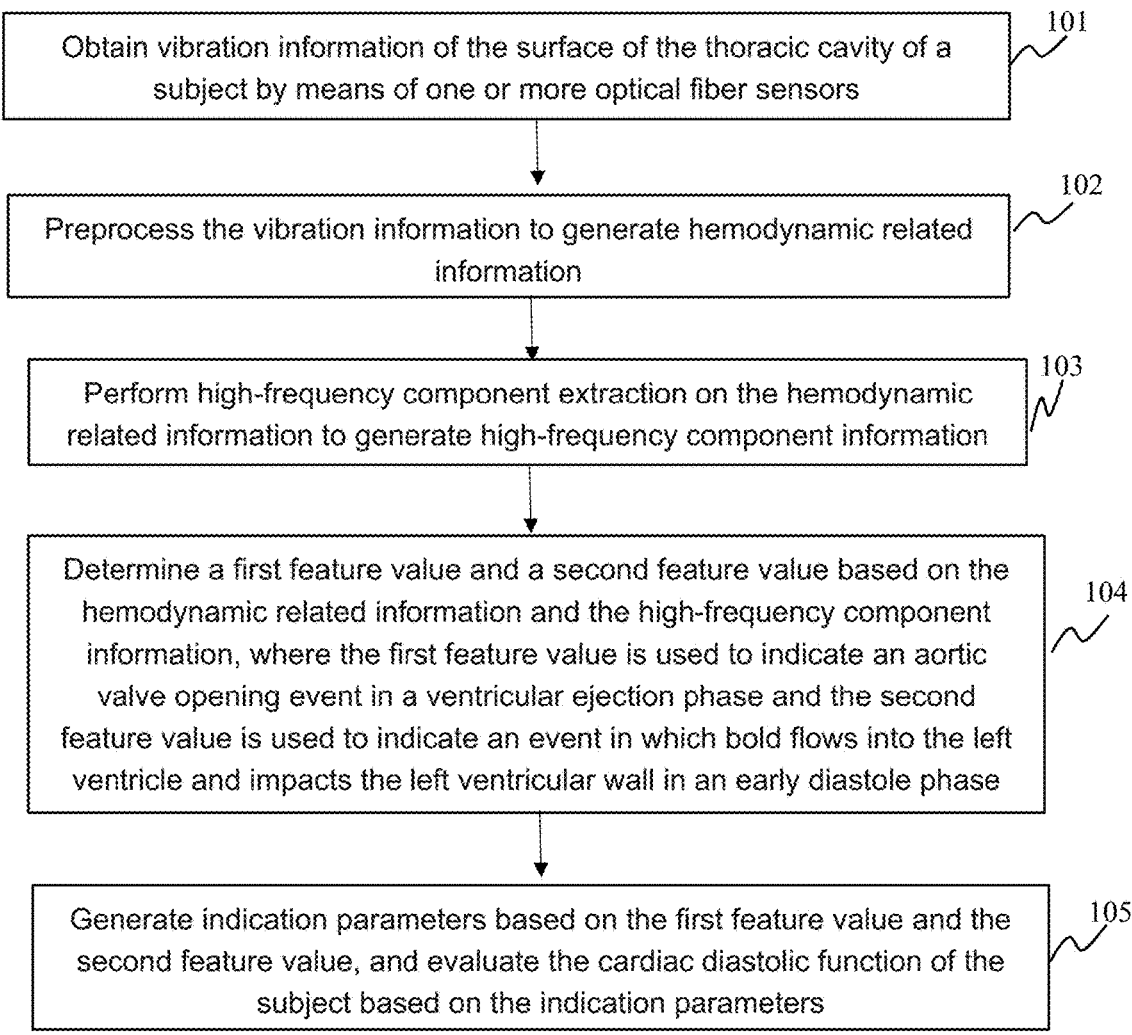
FIG. 1 is a flowchart of a method for evaluating cardiac diastolic function in accordance with a first embodiment of the present invention.

Referring to FIG. 1, a cardiac diastolic function assessment method 100 provided in the first embodiment of the present invention comprises the following steps of S101 to S105. It should be noted that if there are substantially the same results, the diastolic function assessment method of the present invention is not limited to the flowchart sequence shown in

FIG. 1.

S101: acquiring vibration information on a body surface corresponding to a subject's thoracic cavity by means of one or more fiber-optical sensors.

Acquiring vibration information on a body surface corresponding to a subject's thoracic cavity using a fiber-optic sensor, where the fiber-optic sensor can be placed under the subject's body. For example, the subject can be in a posture such as supine, prone, side-lying, etc. The fiber-optic sensor can be placed on the bed, and the subject is supine (prone or side-lying) on it. Taking the subject in a supine position as an example, the preferable measurement position is that the fiber-optic sensor is placed under the subject's back, for example, under the back corresponding to the first thoracic vertebra to the twelfth thoracic vertebra, specifically under the body surface area corresponding to the right shoulder blade. For ease of description, the shoulders of the subject are defined as the left, middle and right shoulders, where the left shoulder includes the body surface area corresponding to the subject's left shoulder blade, the right shoulder includes the body surface area corresponding to the subject's right shoulder blade, and the middle shoulder includes the body surface area between the left and right shoulders. Those of ordinary skill in the art can understand that when the subject lies in the prone position, corresponding to the measurement position when the subject is in the supine posture, the subject's chest is the measurement position corresponding to the back of the subject in the supine position. In addition, the fiber-optic sensor can also be placed on the contact surface behind the back of the subject in the supine posture at a certain tilt angle, or be placed on the contact surface behind the back of the subject leaning on a wheelchair or other leaning objects to acquire the vibration information.

At least one fiber-optical sensor is used for acquiring vibration information, the fiber-optic sensor has a sensing area of at least 20 square centimeters, for example, has a size of 5 cm*4 cm. The sensing area here refers to the area where the optical fibers are distributed in the fiber-optical sensor. When the fiber-optical sensor is placed under the body corresponding to the subject's right shoulder blade, its sensing area covers the body surface area corresponding to the subject's right shoulder blade.

Figure 2:
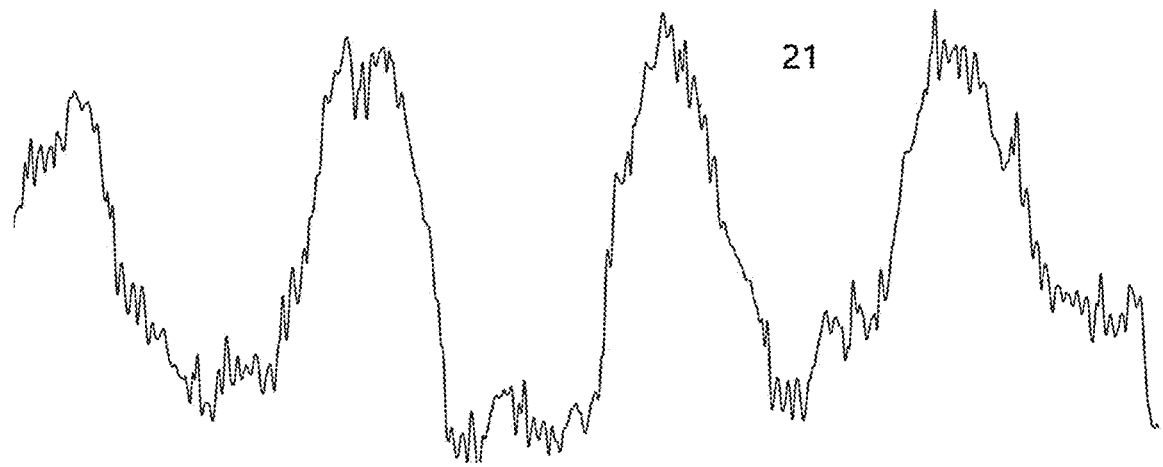
FIG. 2 is a waveform diagram of vibration information of the subject A acquired by a fiber-optic sensor.

FIG. 2 shows a waveform diagram of vibration information of the subject A acquired by a fiber-optic sensor, where the horizontal axis of the curve 21 represents time, and the vertical axis represents normalized vibration information, which is dimensionless. The vibration information acquired by the fiber-optic sensor includes respiratory signal component, the hemodynamic signal component, the interferences caused by environmental micro-vibration and body movement, as well as the noise of the circuit itself. The large outline of the signal at this time is the respiration envelope, and the hemodynamic signal, interference and noise are superimposed on the respiration envelope curve.

S102: preprocessing the vibration information to generate hemodynamic-related information.

The vibration information obtained by different sensors contains different kinds of information, some contains relatively rich information, thus need to be preprocessed to obtain desired signals. For example, when a fiber-optic sensor is used as the vibration sensor, the acquired vibration information contains the subject's respiratory signal, body motion signal, hemodynamic signal, and inherent noise of the sensor.

In the first embodiment of the present invention, S102 may specifically comprise:

performing at least one of: filtering, noise removal and signal scaling on the vibration information to obtain hemodynamic related information; specifically, according to the desired characteristics of the filtered signal, filtering the vibration information to remove noise using one or more of: IIR filter, FIR filter, wavelet filter, zero-phase bidirectional filter, polynomial smoothing filter, integral transform, and differential transformation. For example, filtering the vibration information below 1 Hz to remove respiratory signals and body motion signals. Preprocessing may also comprise steps of: determining whether the vibration information carrying power-line interference, and if yes, using a power frequency filter to remove power-line interference; or, further, removing high-frequency interference (for example, above 45 Hz). The processed information can be scaled according to specific conditions to obtain hemodynamic related information. Or, filtering the vibration signal by directly setting a filter interval such as an interval between 1 Hz-50 Hz.

Figure 3:
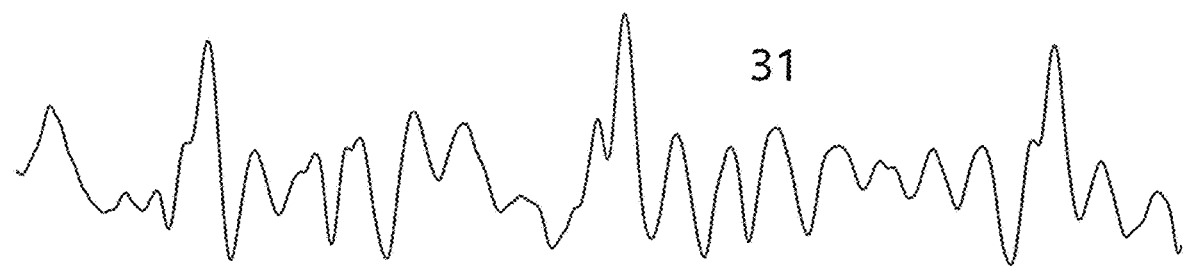
FIG. 3 is a diagram of time-domain waveforms of hemodynamic related information.

FIG. 3 illustrates a time-domain waveform diagram of hemodynamic related information after preprocessing the vibration information of FIG. 2 acquired by the fiber-optic sensor, and a filtering interval of the curve 31 is 2 Hz-45 Hz. Each waveform of the curve 31 has obvious characteristics and good consistency, regular periodicity, clear outline, and stable baseline, that is, the signal quality is better.

S103, performing high-frequency component extraction on the hemodynamic related information to generate high-frequency component information.

A cycle beating of the heart will cause periodic phenomena of various changes, such as periodic changes in intracardiac pressure and cardiovascular pressure, the volume of both atria and the ventricles, opening and closing of the heart valves (including mitral valve, tricuspid valve, aortic valve, pulmonary artery), and blood flow velocity, etc. These periodic changes drive blood flowing in a certain direction in the blood vessels. Hemodynamics studies the mechanics of blood flow in the cardiovascular system, and takes blood flow and the blood vessel deformation as the research object. The "hemodynamic related information" described in the present invention refers to any information related to hemodynamic, and may comprise, but is not limited to, one or more of: information related to producing blood flow (for example, atrial systole and relaxation causes ejection), information related to the dynamics of blood flow (such as CO (cardiac output), left ventricular ejection impacting the aortic arch), information related to blood flow pressure (such as systolic blood pressure, diastolic blood pressure, mean arterial pressure), and blood vessel-related information (such as blood vessel elasticity, etc.). The periodic beating of the heart can maintain blood circulation. Therefore, various parameters related to heartbeats, such as the opening and closing of the heart valve, changes in the volume of both the atria and ventricles, changes in the pressures of the atria and the ventricles, and the flow rate and direction of blood flow in the atria and ventricles. et., which are all hemodynamic related information.

The vibration information obtained through the fiber-optic sensor essentially corresponds to displacement changes, which are relatively smooth. Some details changes in acceleration or velocity are difficult to identify in the displacement change information. For example, the velocity gradually increases from zero to a certain peak value, and then gradually decreases from the peak value to zero; the velocity change curve forms a waveform that first rises and then drops, but the displacement change curve is a monotonous waveform. Therefore, compared to the signal component corresponding to the displacement, the peak-to-valley time widths of the signal components corresponding to the velocity and acceleration is narrower, which may be called high-frequency component information. The high-frequency component extraction method can comprise performing polynomial regression and smoothing, or performing differentiation processing on hemodynamic related information to generate high-frequency component information. For example, S103 may perform second-order differential processing on the hemodynamic related information to generate high-frequency component information.

Figure 4:
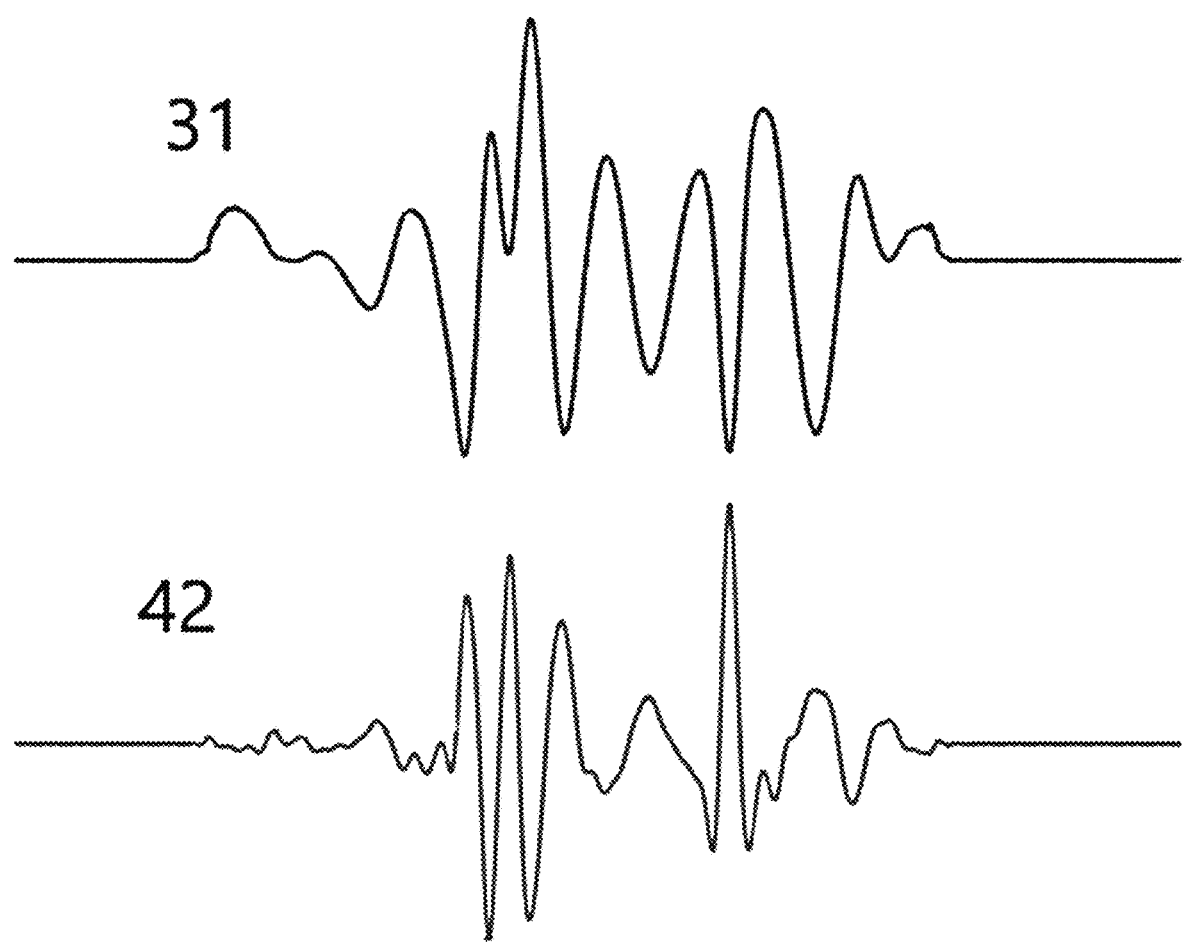
FIG. 4 is a diagram of time-domain waveforms of the hemodynamic related information and high-frequency component information on the same time axis.

As shown in FIG. 4, the curve 42 is a time-domain waveform curve of high-frequency component information. The horizontal axis represents time, and the vertical axis is dimensionless. The waveform curve 42 is obtained by performing second-order differential processing on the waveform curve in one cardiac cycle of the curve 31 of the hemodynamic related information shown in FIG. 3. For comparison, curve 31 and curve 42 are simultaneously illustrated on the same time axis.

S104, determining a first characteristic value and a second characteristic value based on the hemodynamic related information and the high-frequency component information; where the first characteristic value represents an event of aortic valve opening during the ventricular ejection, and the second characteristic value represents an event that blood flows into the left ventricle and impacts the left ventricular wall in the early ventricular diastole.

In the first embodiment, S104 may specifically comprises the following steps of S1041 to S1044.

S1041: synchronizing the hemodynamic related information and the high-frequency component information on the same time axis, and performing heartbeat segmentation.

In some examples, when the vibration information is continuously acquired, the hemodynamic related information, the high-frequency component information, and the vibration energy information which are generated by processing the vibration information are also continuous data, thereby heartbeat segmentation is needed. The heartbeat segmentation can be performed based on the repetitive characteristics in the waveforms of the hemodynamic related information or the high-frequency component information. Since the heart activity has obvious periodicity, there are some obvious characteristics with high repetitiveness. For example, the cardiac cycle of a normal person is between 0.6 s and 1 s, a search interval can be set accordingly, then search for the highest peak, and use the highest peak as a heartbeat segmentation feature. Similarly, the lowest valley can also be used as a heartbeat segmentation feature.

While obtaining the vibration information of the subject, the ECG information can be obtained through the ECG sensor. Because the ECG signal has low noise and clean signals, can be used for heartbeat segmentation with high accuracy. Therefore, the hemodynamic related information and the high-frequency component information can be segmented into heartbeats based on the ECG signals obtained synchronously with the vibration information.

In other examples, when the vibration information is obtained discretely in units of a cardiac cycle, heartbeat segmentation is not necessary, and S1041 can be omitted. In the first embodiment of the present invention, a subsequent processing can comprise: processing the hemodynamic related information and the high-frequency component information in each heartbeat. The subsequent processing can also comprise: performing data superposition and average on the hemodynamic related information or the high-frequency component information according to the heartbeats within a preset period (for example, 5 minutes or 30 minutes) to obtain the corresponding average information, and then performing a subsequent processing on the average information. Therefore, the hemodynamic related information and the high-frequency component information described below can refer to the data in a heartbeat, or the data obtained by superimposing and averaging according to the heartbeats within a preset period.

S1042, dividing a first wave group and a second wave group on the high-frequency component information.

Figure 5:
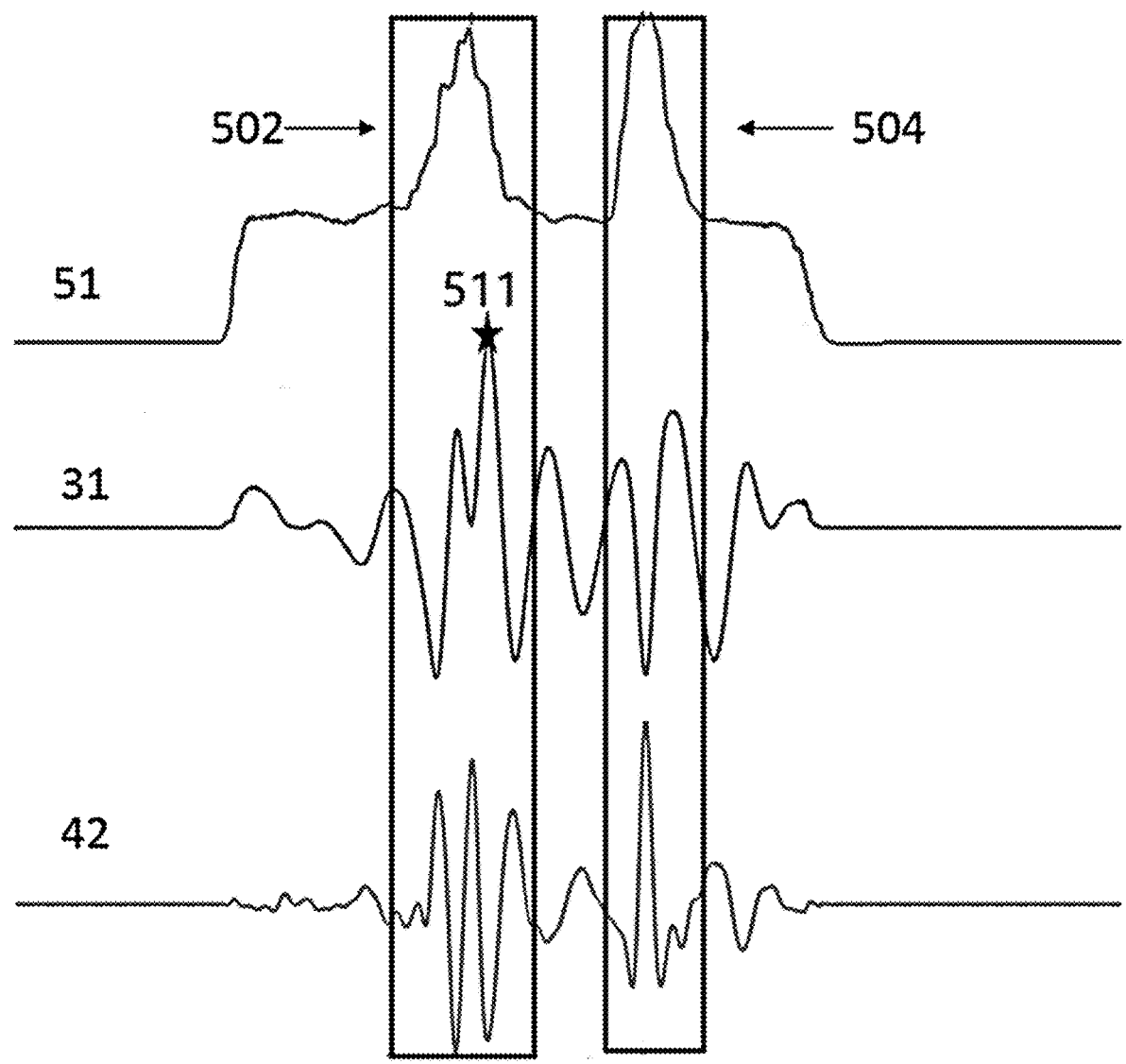
FIG. 5 is a diagram of a first wave group and a second wave group of the hemodynamic related information and the high-frequency component information in a cardiac cycle.

First, generating vibration energy information based on the hemodynamic related information. Specifically, generating vibration energy information by calculating the energy integral of the hemodynamic related information point by point in a specified time window. A time width of the time window for energy integral can be 10 ms, 50 ms, 100 ms or other suitable widths, and the energy integral can be an absolute value, a square, a square root, or other calculation methods after taking the average value. The curve 51 in FIG. 5 is the waveform curve of the vibration energy information in one cardiac cycle. The vibration energy curve has two energy envelopes, which represent the energy accumulation generated during the systolic and diastolic processes of the heart.

Second, determining the highest peak of the hemodynamic related information curve in the same cardiac cycle, as shown by the point 511 in FIG. 5, where the highest peaks represent the shock caused by blood flowing into the aortic arch after aortic ejection; determining one energy envelope containing the point 511 as the first energy envelope, and the other energy envelope as the second energy envelope; determining a time window corresponding to the first energy envelope as the first-time window, and a time window corresponding to the second energy envelope as the second time window.

Finally, determining a first wave group as the wave cluster of the high-frequency component information in the first-time window, and determining a second wave group as the wave cluster of the high-frequency component information in the second time window. As shown in FIG. 5, it is a diagram of wave group division, for example, in one cardiac cycle. Where the curves 31 and 42 are the same as those shown in FIG. 4, the curve 51 is the waveform curve of the vibration energy information. The wave cluster of the curve 42 in the box area 502 is the first wave group, and the wave cluster of the curve 42 in the box area 504 is the second wave group.

In some embodiments, wave group division may also be auxiliary based on ECG information. While acquire the vibration information of the subject, and acquire ECG information through an ECG sensor; and determine a first wave group and a second wave group auxiliary based on the ECG information. For example, the time of the first wave group and the QRS wave group of the ECG information almost corresponds in the same cardiac cycle. The first wave group is usually between 80 milliseconds and 200 milliseconds after the Q wave of the ECG information; thus, the ECG information can be used to assist in determining the first wave group.

In some embodiments, the wave group division may also be based on heart sound information. While acquire the vibration information of the subject, acquire the heart sound information by means of a heart sound sensor, and then determine the first wave group and the second wave group based on the heart sound information. For example, determining a first wave group as the wave cluster of the curve 42 that are synchronized with the duration of the first heart sound, and determining a second wave group as the wave cluster of the curve 42 that are synchronized with the duration of the second heart sound.

Figure 6:
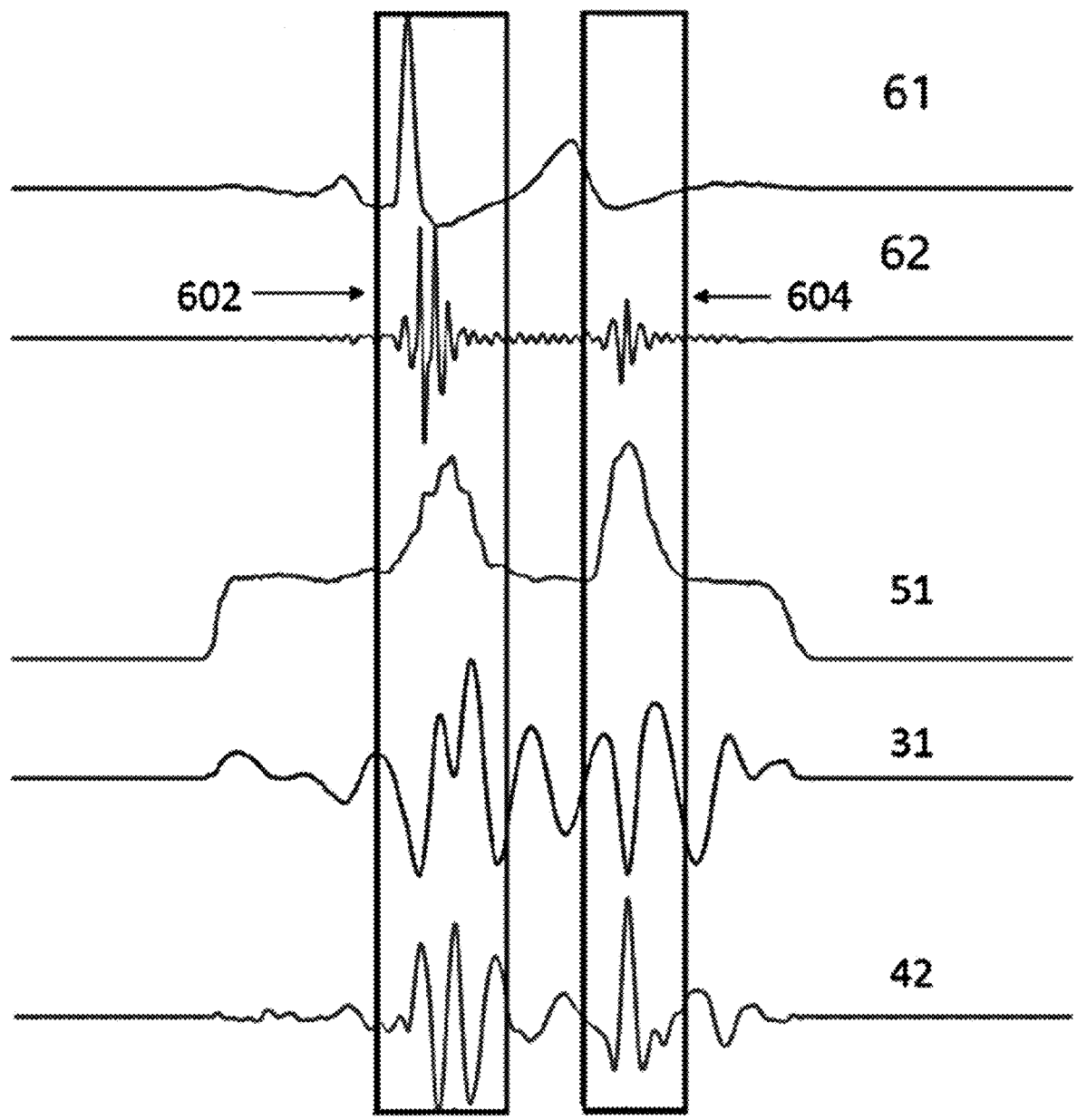
FIG. 6 is a diagram of dividing a first wave group and a second wave group using ECG information curve, heart sound information curve, and vibration energy information curve.

As shown in FIG. 6, synchronize the synchronously acquired ECG information, heart sound information, and vibration energy information, as well as the three curves of FIG. 5 on the same time axis; where the curve 61 is ECG information, the curve 62 is heart sound information; therefore, the wave cluster of the curve 42 in the box area 602 is the first wave group, and the wave cluster in the box area 604 is the second wave group.

S1043, searching for "W-shape" wave in the first wave group, and determining a first characteristic value as a falling edge amplitude after a midpoint of the "W-shape" wave.

Figure 7:
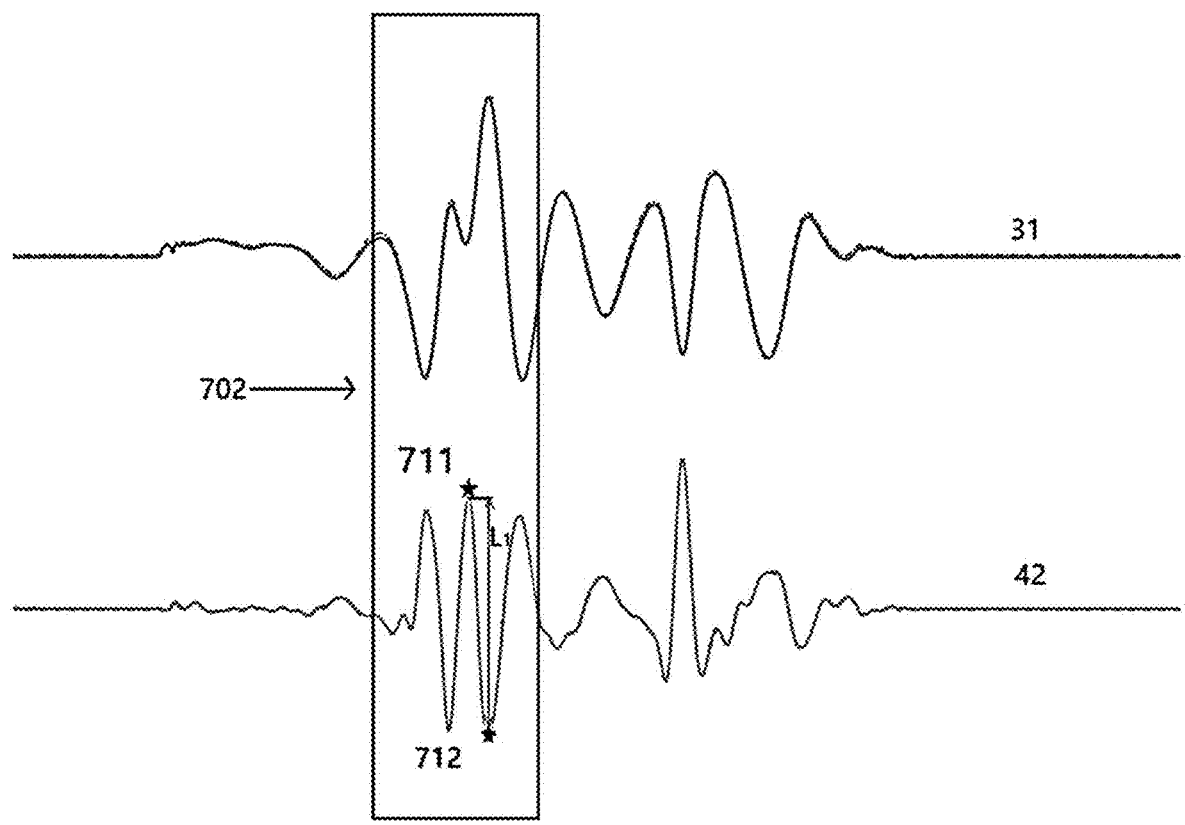
FIG. 7 is a diagram of a first characteristic value.

The midpoint is the symmetrical intersection point of the "W-shape" wave. As shown in FIG. 7, the point 711 is the midpoint of the "W-shape" wave. A falling edge amplitude after the point 711 is determined as the first characteristic value, that is, an amplitude between the point 711 and a first trough 712 thereafter is determined as the first characteristic value L1.

S1044, searching for "W-shape" wave in the second wave group, and determining a second characteristic value as a rising edge of a second wave trough in a subsequent preset time period.

Figure 8:
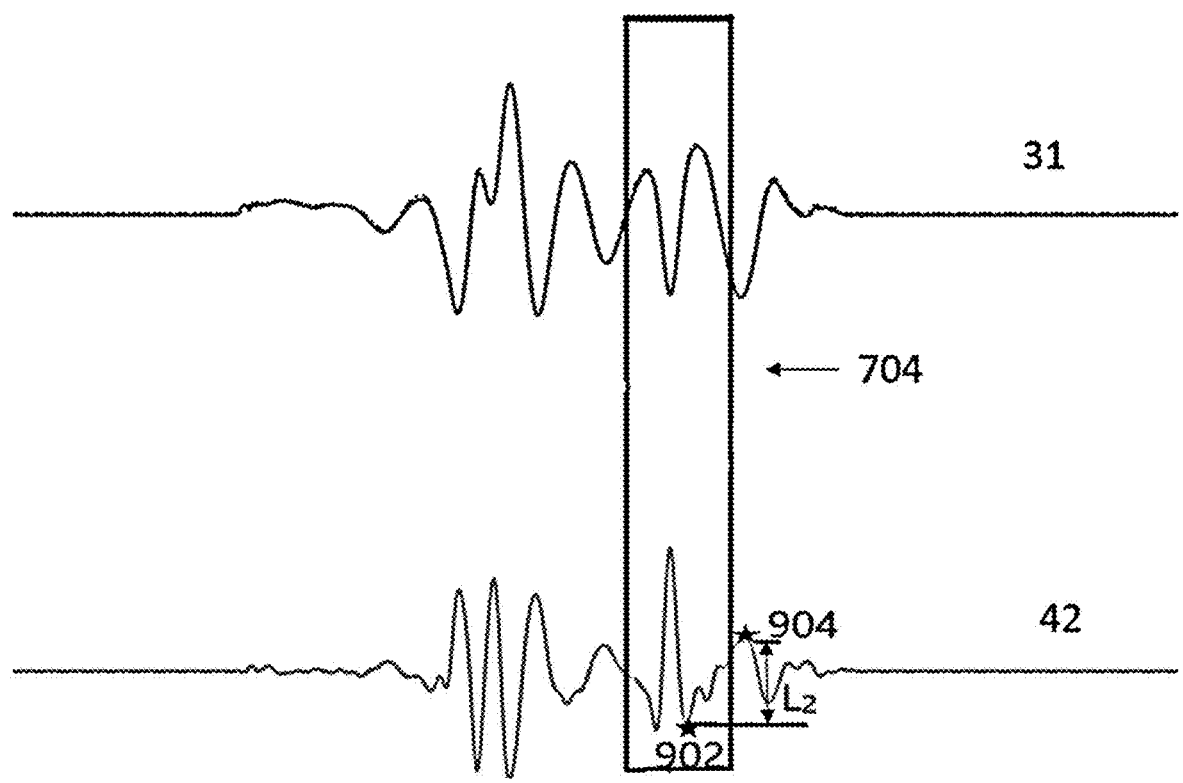
FIG. 8 is a diagram of a second characteristic value.

First, search for "W-shape" wave in the second wave group and determine a second trough thereof, where the second trough represents an event of pulmonary valve closure, as shown in FIG. 8, the point 902 is the second trough. Secondly, determine the highest peak in a preset time period after the second trough, where the preset time period can be any value between 20 milliseconds and 110 milliseconds, and can also be adjusted according to the designated subject group. As shown in FIG. 8, the highest peak in the preset time period after the point 902 is marked as the point 904. Finally, determine an amplitude between the second trough and the highest peak, that is, a rising edge of the point 902 in the preset time period, as the second characteristic value L2.

The event of aortic valve opening during the ventricular ejection and the event that blood flows into the left ventricle and impacts the left ventricular wall in the early ventricular diastole can be obtained by means of different sensors which acquire different kinds of information. For example, an electrophysiological sensor can obtain the electrical signal of the event, and a vibration sensor can obtain the vibration signal of the event. Specifically, a body surface motion of a subject's thoracic cavity can be acquired through the vibration sensor, which can be extracted to obtain the event of aortic valve opening during the ventricular ejection and the event that blood flows into the left ventricle and impacts the left ventricular wall in the early ventricular diastole. The event of aortic valve opening during the ventricular ejection comprises the vibration on the body surface formed by muscle movement and blood flow movement caused by the aortic valve opening during the ventricular ejection; the event that blood flows into the left ventricle and impacts the left ventricular wall in the early ventricular diastole comprises the vibration on the body surface formed by muscle movement and blood flow movement caused by that blood flows into the left ventricle and impacts the left ventricular wall in the early ventricular diastole. In the first embodiment of the present invention, the first characteristic value represents the vibration amplitude on the body surface formed by muscle movement and blood flow movement caused by the aortic valve opening during the ventricular ejection, the second characteristic value represents the vibration amplitude on the body surface formed by muscle movement and blood flow movement caused by that blood flows into the left ventricle and impacts the left ventricular wall in the early ventricular diastole. It is understandable that in addition to vibration amplitude, parameters such as vibration energy, vibration frequency, or vibration time, can also be used to represent the event of aortic valve opening during the ventricular ejection and the event that blood flows into the left ventricle and impacts the left ventricular wall in the early ventricular diastole.

S105, generating indicating parameters based on the first characteristic value and the second characteristic value, and evaluating the cardiac diastolic function of the subject based on the indicating parameters.

In the first embodiment of the present invention, a ratio of the second characteristic value to the first characteristic value may be used as the indicating parameter. When the indicating parameter is greater than a threshold, it is determined that the subject is in an elevated filling pressure state. The elevated filling pressure state refers to the state of the heart if: tricuspid regurgitation velocity>2.8 m/s, E/e'>14, and E/A>1.

Figure 9A:
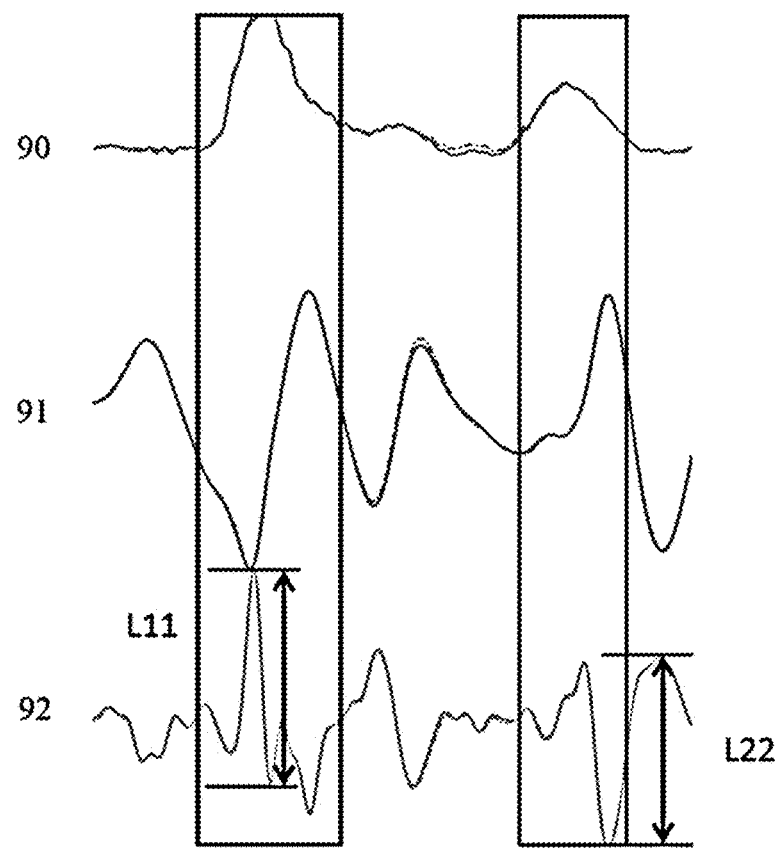
FIG. 9A is a diagram of the first and second characteristic values based on the vibration information of the subject B.

FIG. 9A illustrates the first characteristic value and the second characteristic value according to the vibration information of the thoracic body surface of the subject B. Subject B is a patient with heart failure in a state of elevated filling pressure. In FIG. 9A, the curve 90 is the vibration energy information curve, the curve 91 is the hemodynamic related information curve, and the curve 92 is the high frequency component information curve. L11 is the first characteristic value, and L22 is the second characteristic value. Compared with FIG. 7 and FIG. 8, the second characteristic value of the patient with heart failure has changed greatly. Where a ratio of the second characteristic value and the first characteristic value is used to represent the change.

A person of ordinary skill in the art can obtain a method for evaluating the ventricular filling pressure when the ratio of the first characteristic value to the second characteristic value is used as an indicating parameter, which is also included in the protection scope of the present invention. In addition, those of ordinary skill in the art can easily obtain that the first characteristic value and the second characteristic value can also generate the indicating parameter by other calculations, including but not limited to: addition, subtraction, multiplication, division, exponent, etc., which are also included within the scope of protection of the present invention.

Figure 9B:
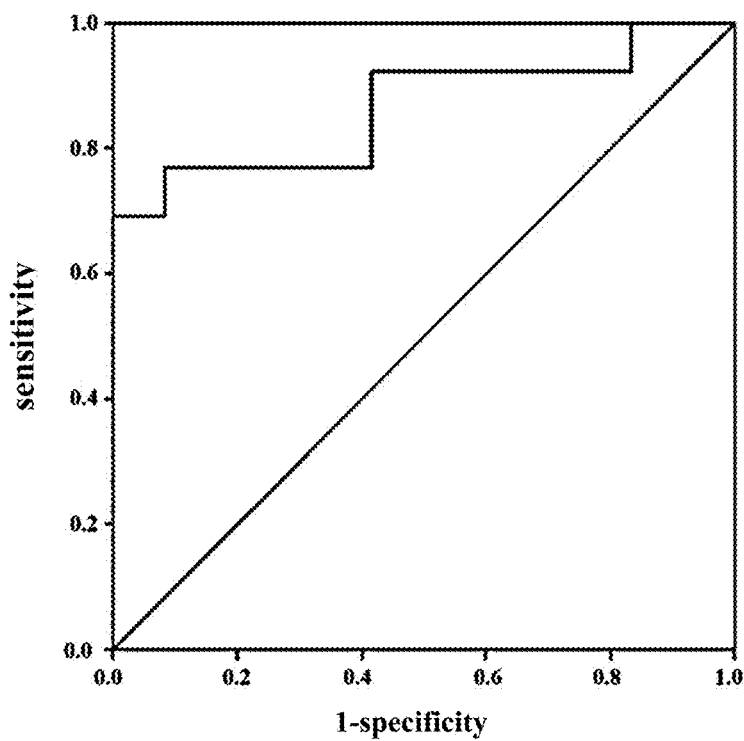
FIG. 9B is an ROC curve of the indicating parameters.

Twenty-five heart failure patients as testing subjects were enrolled in a clinical study, where twelve patients with elevated filling pressure (marked as positive) and thirteen patients with non-elevated filling pressure (marked as negative). According to the above-mentioned cardiac diastolic function assessment method 100, calculates indicating parameters of the twenty-five subjects. Analyze sensitivity and specificity of the indicating parameters for the twenty-five subjects, and construct the ROC curves as shown in FIG. 9B, where an accuracy of the indicated parameter is 86.5%, the sensitivity is 76.9%, and the specificity is 91.7%. A threshold is 0.4015, and the threshold is determined based on people with heart failure. In some embodiments, the threshold may also be an absolute threshold, which is used to distinguish between healthy people and people with cardiac diastolic dysfunction. The threshold may also depend on the subject itself, for example, a relative threshold when diastolic function deteriorates can be obtained on the basis of the analysis of personal history data of the monitored subject.

In the first embodiment of the present invention, the diastolic function is represented by ventricular filling pressure, for example, an elevated filling pressure represents serious diastolic dysfunction. In addition, the diastolic function can also be represented by atrial pressure. The left ventricular filling pressure is related to the left atrial pressure and the pulmonary artery pressure due to the heart structure. Therefore, in some embodiments, the indicating parameters can be used to assess the filling pressure; the indicating parameters after a series of transformation calculation, can also be used to indirectly assess the left atrial pressure, the pulmonary artery pressure, and the degree of heart failure, etc., which are also included within the protection scope of the present invention.

Second Embodiment

The second embodiment of the present invention provides a computer readable storage medium having computer programs stored thereon, which when being executed by a processor, cause the processor to perform the steps of the method for evaluating cardiac diastolic function in accordance with the first embodiment of the present invention.

Third Embodiment

Figure 10:
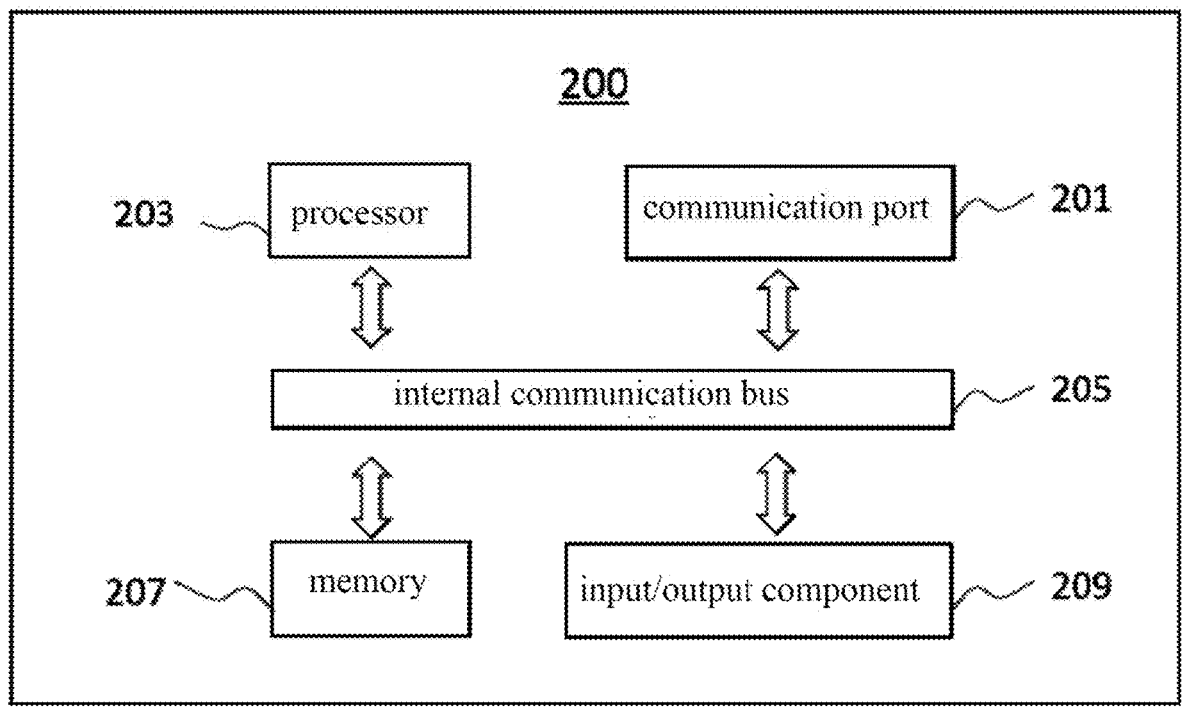
FIG. 10 is a block diagram of a device for evaluating cardiac diastolic function in accordance with a third embodiment of the present invention.

The third embodiment of the present invention provides a device for evaluating cardiac diastolic function. FIG. 10 illustrates a block diagram of a cardiac diastolic function assessment device 200. The device 200 may be a special computer device to process the vibration information acquired by a fiber-optic sensor.

For example, the cardiac diastolic function assessment device 200 may comprise a communication port 201 connected to a network for data communication. The cardiac diastolic function assessment device 200 may further comprise one or more processors 203 for executing computer instructions. The computer instructions may comprise, for example, routines, programs, objects, components, data structures, procedures, modules, and functions that perform the cardiac diastolic function assessment method described herein. For example, the processor 203 can receive the vibration information acquired by means of the fiber-optic sensor, and preprocess the vibration information to generate hemodynamic related information.

In some examples, the processors 203 may comprise one or more hardware processors, such as: a microcontroller, a microprocessor, a Reduced Instruction Set Computer (RISC), an Application Specific Integrated Circuit (ASIC), a Graphics Processing Unit (GPU)), Central Processing Unit (CPU), Digital Signal Processor (DSP), Field Programmable Gate Array (FPGA), Advanced RISC Machine (ARM), and Programmable Logic Device (PLD) etc., or any circuit or processor or a combination thereof capable of performing one or more functions.

The cardiac diastolic function assessment device 200 may comprise an internal communication bus 205, a memory 207 for various data processed and/or sent by the computer, and program instructions stored in other types of non-transitory storage media executed by the processor 203 in the memory 207. The method and/or process of the present invention can be implemented by program instructions. The cardiac diastolic function assessment device 200 also comprises an input/output component 209, which is used for input/output between the computer and other components (for example, User Interface Elements).

For ease of description, only one processor is described in the cardiac diastolic function assessment device 200 of the present invention. However, it should be noted that the cardiac diastolic function assessment device 200 of the present invention may also comprise multiple processors. Therefore, the process and/or method disclosed in the present invention may be executed by one processor as described in the present invention, and can also be executed jointly by multiple processors. For example, if the processor 203 of the cardiac diastolic function assessment device 200 in the present invention performs step A and step B, it should be understood that step A and step B can also be performed jointly or separately by two different processors (For example, a first processor executes step A, a second processor executes step B, or the first and second processors jointly execute steps A and B).

Fourth Embodiment

The fourth embodiment of the present invention provides a cardiac diastolic function assessment system, including:

one or more vibration sensors; and the cardiac diastolic function assessment device provided in the third embodiment of the present invention.

Figure 11:
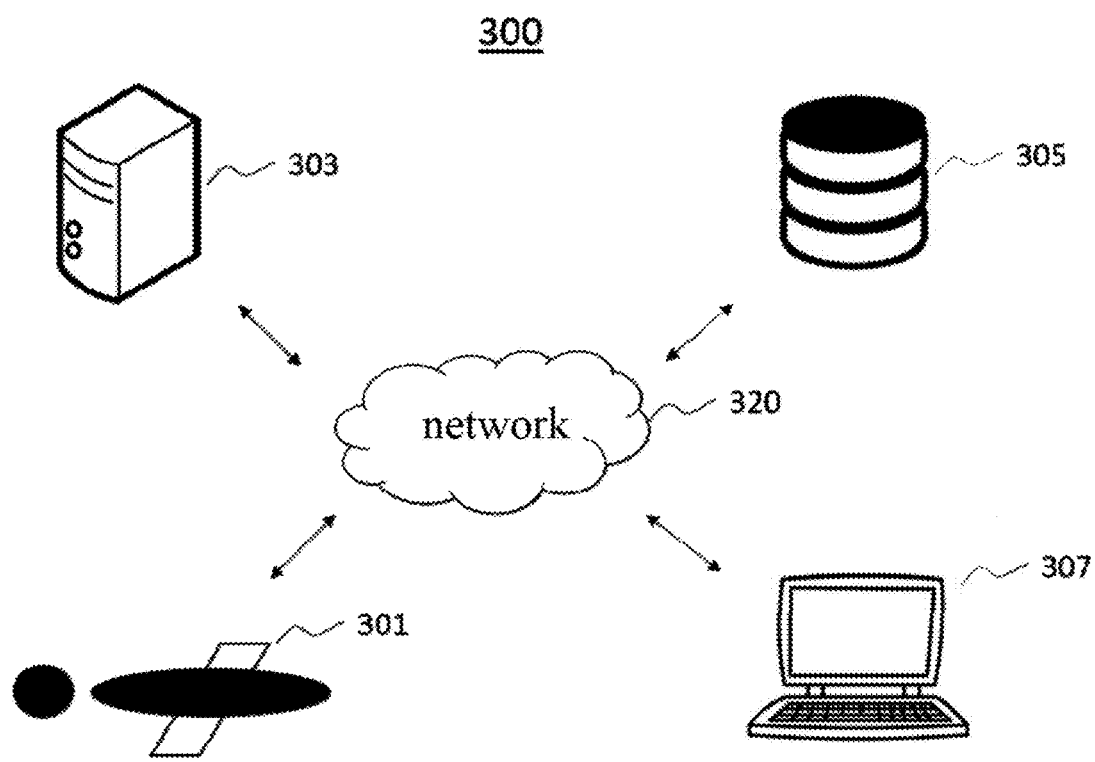
FIG. 11 is a block diagram of a system for evaluating cardiac diastolic function in accordance with a fourth embodiment of the present invention.

FIG. 11 illustrates a block diagram of a cardiac diastolic function assessment system 300. The cardiac diastolic function assessment system 300 may comprise one or more vibration sensors 301, one or more cardiac diastolic function assessment devices 303, and one or more storage devices 305.

The fiber-optic sensor 301 can be placed under the subject's body. For example, the subject can be in a posture such as supine, prone, side-lying, etc. The fiber-optic sensor can be placed on the bed, and the subject is supine (prone or side-lying) on it. Taking the subject in a supine position as an example, a preferable measurement position is that the fiber-optic sensor is placed under the subject's back. Those of ordinary skill in the art can understand that when the subject lies in the prone position, the subject's chest is the measurement position corresponding to the back of the subject in the supine position. In addition, the vibration sensor can also be placed on the contact surface behind the back of the subject in the supine posture at a certain tilt angle or on the contact surface behind the back of the subject leaning on a wheelchair or other leaning objects to acquire the vibration information.

The cardiac diastolic function assessment device 303 as described in the third embodiment of the present invention, can be connected to the vibration sensor 301 through the network 320. The network 320 may be a single network, such as a wired network or a wireless network, or a combination of multiple networks. The network 320 may comprise, but is not limited to, a Local Area Network, a Wide Area Network, a shared internet, a dedicated internet, and the like. The network 320 may comprise a variety of network access points, such as wireless or wired access points, base stations, or network access points, through which other components of the diastolic function assessment system 300 can connect to the network 320 and transmit information through the network.

The storage device 305 may be configured to store data and instructions. The storage device 305 may comprise, but is not limited to, Random Access Memory, Read Only Memory, Programmable Read Only Memory, and the like. The storage device 305 may store information using electrical energy, magnetic energy, or optical methods, such as Hard Disks, Floppy Disks, Magnetic Core Memories, CDs, DVDs, and the like. The storage devices mentioned above are just a few examples, and the storage devices used by the storage device 305 are not limited to these.

In some examples, the diastolic function assessment system 300 may further comprise an output device 307. The output device 307 is used to output the result of the diastolic function assessment, and the output methods comprise but are not limited to graphics, text, data, voice, etc., such as one or more of graphic display, digital display, voice broadcast, braille display, etc. The output device 307 may be one or more of: a display, a mobile phone, a tablet computer, a projector, a wearable device (watch, earphone, glasses, etc.), a braille display, or the like. In some examples, the output device 307 can display the diastolic function assessment result of the subject in real time. In other examples, the output device 307 can display a report in non-real time, which is the measurement result of the subject in a preset time period, for example, the user's filling pressure monitoring results during the sleeping time period. When monitor a subject with heart failure, if a state of elevated filling pressure is assessed by the diastolic function assessment device, the subject with heart failure will face a worsening heart failure at this time and need to be hospitalized. The output device of the monitoring system can send reminders to the patient with heart failure, such as sending text messages, emails, phone calls, WeChat, and other instant messages; and can also send a message to the family doctor of the patient with heart failure, prompt that the patient may suffer from worsening heart failure to help doctors to make decisions. The system may further comprise a doctor-patient communication platform, and when the doctor receives the system notification that the patient may suffer from worsening heart failure, he can communicate with the patient in time.

For another example, the output device 307 can also send an early warning, for example, a voice warning. When the device evaluates the diastolic function of the patient with heart failure being a state of elevated filling pressure, the patient with heart failure will suffer from worsening heart failure at this time, and the system can remind the patient to see a doctor in time by voice warning.

The method of the present invention monitors the diastolic function by acquiring the vibration information of the subject without intruding his body, it is a passively measuring, and can realize continuous monitoring. The subject only needs to lie on the measuring device to perform the measurement, and no need for professional assistance. The method has the advantages of high measurement accuracy and simple operation, can improve the comfort of the tester, and can be applied to scenes such as hospitals and homes. The diastolic function assessment system provided in the present invention can evaluate the diastolic function of the subject, and then prompt a warning in advance when deterioration appear, so as to help the subject avoid deterioration.

A person of ordinary skill in the art can understand that all or part of the steps in the various methods of the above-mentioned embodiments can be completed by a program instructing relevant hardware. The program can be stored in a computer-readable storage medium. The computer-readable storage medium may comprise: ROM (Read Only Memory), RAM (Random Access Memory), magnetic disk or optical disk, etc.

The foregoing descriptions are only preferable embodiments of the present invention, and are not intended to limit the present invention. Any modification, equivalent replacement, and improvement made within the spirit and principle of the present invention shall be included in the protection scope of the present invention.

What is claimed is:

1. A diastolic function assessment method, comprising to steps of:
   acquiring vibration information on a body surface corresponding to thoracic cavity of a subject by means of one or more fiber-optic sensors which are placed under the body of the subject;
   preprocessing the vibration information to generate hemodynamic related information;
   performing high-frequency component extraction on the hemodynamic related information to generate high-frequency component information; comprising a step of:
     performing second-order differential processing on the hemodynamic related information to generate high-frequency component information; or
     performing polynomial regression and smoothing on the hemodynamic related information to generate high-frequency component information;

determining a first characteristic value and a second characteristic value based on the hemodynamic related information and the high-frequency component information; where the first characteristic value represents an event of aortic valve opening during the ventricular ejection, and the second characteristic value represents an event that blood flows into the left ventricle and impacts the left ventricular wall in the early ventricular diastole; wherein the event of aortic valve opening during the ventricular ejection comprises vibration on the body surface formed by muscle movement and blood flow movement caused by the aortic valve opening during the ventricular ejection; the event that blood flows into the left ventricle and impacts the left ventricular wall in the early ventricular diastole comprises vibration on the body surface formed by muscle movement and blood flow movement caused by that blood flows into the left ventricle and impacts the left ventricular wall in the early ventricular diastole; the first characteristic value represents a vibration amplitude on the body surface formed by muscle movement and blood flow movement caused by the aortic valve opening during the ventricular ejection, the second characteristic value represents a vibration amplitude on the body surface formed by muscle movement and blood flow movement caused by that blood flows into the left ventricle and impacts the left ventricular wall in the early ventricular diastole; and generating indicating parameters based on the first characteristic value and the second characteristic value, and evaluating the cardiac diastolic function of the subject based on the indicating parameters.

2. The method of claim 1, wherein the one or more fiber-optic sensors are configured to be placed under the body surface corresponding to the first thoracic vertebra to the twelfth thoracic vertebra of the subject;
a sensing area of the one or more fiber-optic sensors is at least 20 square centimeters;
one of the body positions of the subject is supine.

3. The method of claim 2, wherein the one or more fiber-optic sensors are configured to be placed under the body surface corresponding to the right shoulder blade of the subject;
the sensing area of the one or more fiber-optic sensors covers the body surface area corresponding to the right shoulder blade of the subject.

4. The method of claim 1, wherein the step of determining a first characteristic value and a second characteristic value based on the hemodynamic related information and the high-frequency component information, comprises steps of:
generating vibration energy information based on the hemodynamic related information, where the vibration energy information comprises two energy envelopes in one cardiac cycle;
synchronizing the hemodynamic related information and the vibration energy information on the same time axis;
determining the highest peak of the hemodynamic related information in the same cardiac cycle;
determining a duration of one energy envelope including the highest peak of the hemodynamic related information as a first-time window, and a duration of the other energy envelope as a second time window;
determining wave clusters of the high-frequency component information within the first-time window as a first wave group, wave clusters of the high-frequency component information within the second time window as a second wave group; and determining a first characteristic value and a second characteristic value based on the first wave group and the second wave group.

5. The method of claim 4, further comprising steps of:
acquiring ECG information of the subject by means of an ECG sensor in synchronization with the vibration information; and
determining a first wave group of the high-frequency component information auxiliary based on a QRS complex of the ECG information.

6. The method of claim 4, wherein the step of determining a first characteristic value and a second characteristic value based on the first wave group and the second wave group, comprises steps of:
searching for "W-shape" wave in the first wave group, and determining a first characteristic value as a falling edge amplitude after a midpoint of the "W-shape" wave; and
searching for "W-shape" wave in the second wave group, and determining a second characteristic value as a rising edge amplitude of a second wave trough in a subsequent preset time period.

7. The method of claim 1, wherein evaluating the cardiac diastolic function of the subject based on the indicating parameters, comprises: evaluating the subject's ventricular filling pressure as an elevated filling pressure or a non-elevated filling pressure based on the indicating parameters; and for the subject with elevated filling pressure: tricuspid regurgitation velocity>2.8 m/s, E/e'>14, and E/A>1.

8. The method of claim 7, wherein evaluating the subject's ventricular filling pressure, comprising steps of:
calculating a ratio of the second characteristic value to the first characteristic value as an indicating parameter; and
identifying the subject with elevated filling pressure if the indicating parameter is greater than a threshold.

9. The method of claim 8, wherein the threshold is 0.4015; or
the threshold depends on a certain people group.

10. The method of claim 1, wherein the hemodynamic related information is:
data in one cardiac cycle; or
data that is superimposed and averaged in a unit of cardiac cycle within a preset time period.

11. A non-transitory computer-readable storage medium having one or more computer programs stored thereon, wherein when the one or more computer programs are executed by a processor, causes the processor to perform the steps of the diastolic function assessment method of claim 1.

12. A diastolic function assessment device, comprising:
one or more processors;
a memory; and
one or more computer programs stored in the memory and configured to be executed by the one or more processors; wherein when the one or more computer programs are executed by the one or more processors, causes the one or more processors to perform the steps of the diastolic function assessment method of claim 1.

13. A diastolic function assessment system, comprising:
one or more fiber-optic sensors configured to be placed under the body of a subject for acquiring vibration information on a body surface corresponding to the thoracic cavity of the subject; and
a diastolic function assessment device, connected to the one or more fiber-optic sensors, and comprising:
one or more processors;
a memory; and
one or more computer programs stored in the memory and configured to be executed by the one or more processors; wherein when the one or more computer programs are executed by the one or more processors, causes the one or more processors to perform a diastolic function assessment method, comprising steps of:

acquiring vibration information on a body surface corresponding to thoracic cavity of a subject by means of one or more fiber-optic sensors which are placed under the body of the subject;

preprocessing the vibration information to generate hemodynamic related information;

performing high-frequency component extraction on the hemodynamic related information to generate high-frequency component information; comprising a step of:

performing second-order differential processing on the hemodynamic related information to generate high-frequency component information; or performing polynomial regression and smoothing on the hemodynamic related information to generate high-frequency component information;

determining a first characteristic value and a second characteristic value based on the hemodynamic related information and the high-frequency component information; where the first characteristic value represents an event of aortic valve opening during the ventricular ejection, and the second characteristic value represents an event that blood flows into the left ventricle and impacts the left ventricular wall in the early ventricular diastole; wherein the event of aortic valve opening during the ventricular ejection comprises vibration on the body surface formed by muscle movement and blood flow movement caused by the aortic valve opening during the ventricular ejection; the event that blood flows into the left ventricle and impacts the left ventricular wall in the early ventricular diastole comprises vibration on the body surface formed by muscle movement and blood flow movement caused by that blood flows into the left ventricle and impacts the left ventricular wall in the early ventricular diastole; the first characteristic value represents a vibration amplitude on the body surface formed by muscle movement and blood flow movement caused by the aortic valve opening during the ventricular ejection, the second characteristic value represents a vibration amplitude on the body surface formed by muscle movement and blood flow movement caused by that blood flows into the left ventricle and impacts the left ventricular wall in the early ventricular diastole; and generating indicating parameters based on the first characteristic value and the second characteristic value, and evaluating the cardiac diastolic function of the subject based on the indicating parameters.

14. A diastolic function assessment system based on machine learning, comprising:

one or more processors, which are centrally or individually programmed to perform the steps of:

receiving vibration information on a body surface corresponding to a subject's thoracic cavity as input information for training;

analyzing the input information for training to establish an assessment model by machine learning, and;

receiving vibration information on a body surface corresponding to a tested subject's thoracic cavity; and performing an assessment to the tested subject's diastolic function by the assessment model;

wherein the assessment model performs steps of:

preprocessing the vibration information to generate hemodynamic related information;

performing high-frequency component extraction on the hemodynamic related information to generate high-frequency component information; comprising a step of:

performing second-order differential processing on the hemodynamic related information to generate high-frequency component information; or performing polynomial regression and smoothing on the hemodynamic related information to generate high-frequency component information;

determining a first characteristic value and a second characteristic value based on the hemodynamic related information and the high-frequency component information; where the first characteristic value represents an event of aortic valve opening during the ventricular ejection, and the second characteristic value represents an event that blood flows into the left ventricle and impacts the left ventricular wall in the early ventricular diastole; wherein the event of aortic valve opening during the ventricular ejection comprises vibration on the body surface formed by muscle movement and blood flow movement caused by the aortic valve opening during the ventricular ejection; the event that blood flows into the left ventricle and impacts the left ventricular wall in the early ventricular diastole comprises vibration on the body surface formed by muscle movement and blood flow movement caused by that blood flows into the left ventricle and impacts the left ventricular wall in the early ventricular diastole; the first characteristic value represents a vibration amplitude on the body surface formed by muscle movement and blood flow movement caused by the aortic valve opening during the ventricular ejection, the second characteristic value represents a vibration amplitude on the body surface formed by muscle movement and blood flow movement caused by that blood flows into the left ventricle and impacts the left ventricular wall in the early ventricular diastole; and generating indicating parameters based on the first characteristic value and the second characteristic value, and evaluating the cardiac diastolic function of the tested subject based on the indicating parameters.

\* \* \* \* \*